United States Patent [19] [11] 4,200,739
Kelly [45] Apr. 29, 1980

[54] ENLARGED-HETERO-RING PROSTACYCLIN ANALOGS

[75] Inventor: Robert C. Kelly, Kalamazoo, Mich.

[73] Assignee: The Upjohn Company, Kalamazoo, Mich.

[21] Appl. No.: 935,392

[22] Filed: Aug. 21, 1978

Related U.S. Application Data

[60] Division of Ser. No. 819,941, Jul. 28, 1977, Pat. No. 4,124,599, which is a continuation-in-part of Ser. No. 725,547, Sep. 22, 1976, abandoned, which is a continuation-in-part of Ser. No. 716,777, Aug. 23, 1976, abandoned.

[51] Int. Cl.$^2$ .................................. C07D 311/02
[52] U.S. Cl. ........................ 542/426; 260/345.2
[58] Field of Search ............ 260/345.2; 542/426, 542/439

[56] References Cited
PUBLICATIONS

Pace-Asciak et al., Biochem., 10, 3657 (1971).
Pace-Asciak et al., JACS, 98, 2348 (1976).

Primary Examiner—Nicky Chan
Attorney, Agent, or Firm—Morris L. Nielsen; Robert A. Armitage

[57] ABSTRACT

Prostaglandin (PG$_1$) derivatives having (1) a 6-keto feature, together with a 9-deoxy-9-hydroxymethyl feature for example

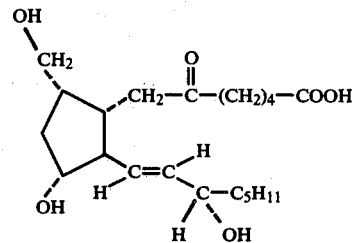

or (2) a 9-deoxy-6,9-epoxymethano feature together with a 5-halo or 6-hydroxy feature, for example

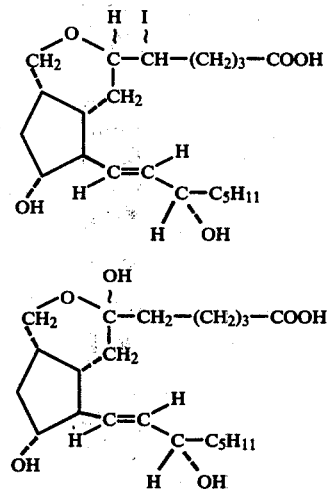

or a 5,6-didehydro feature, for example in an enol ether of the formula

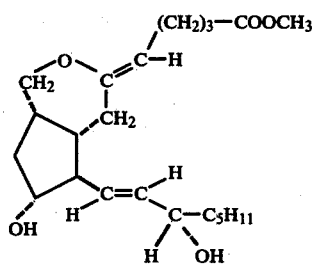

said derivatives having pharmacological activity. Processes for preparing them and the appropriate intermediates are disclosed.

17 Claims, No Drawings

ENLARGED-HETERO-RING PROSTACYCLIN ANALOGS

CROSS REFERENCE TO RELATED APPLICATIONS

This application is a division of then copending application Ser. No. 819,941 filed July 28, 1977, now issued as U.S. Pat. No. 4,124,599, which was a continuation-in-part of then copending application Ser. No. 725,547 filed Sept. 22, 1976, since abandoned, which was a continuation-in-part of then copending application Ser. No. 716,777 filed Aug. 23, 1976, since abandoned.

INCORPORATION BY REFERENCE

The essential material for this application, including the background of the invention, the disclosure of the invention, and the description of the preferred embodiments, including Preparations and Examples, is incorporated by reference from issued U.S. Pat. No. 4,124,599, under the provisions of M.P.E.P. 608.01(p).

BACKGROUND OF THE INVENTION

This invention relates to prostaglandin derivatives and to a process for preparing them.

The prostaglandins and analogs are well-known organic compounds derived from prostanoic acid which has the following structure and atom numbering:

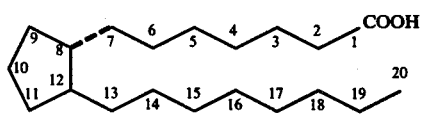

As drawn hereinafter the formulas represent a particular optically active isomer having the same absolute configuration as $PGE_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background on prostaglandins, see for example Bergstrom et al., Pharmacol. Rev. 20, 1 (1968). For related compounds see Pace-Asciak et al., Biochem. 10, 3657 (1971). Related compounds are described in a publication on 6-keto-prostaglandin $F_{1\alpha}$ by Pace-Asciak, J. Am. Chem. Soc. 98, 2348 (1976) and a publication on "PGX" (6,9α-oxido-9α,15α-dihydroxyprosta-(Z)5, (E)13-dienoic acid) by E. J. Corey et al., J. Am. Chem. Soc. 99, 20006 (1977).

Some of the compounds of this invention may be regarded as analogs of prostacyclin and prostacyclin-type compounds.

Prostacyclin, an organic compound related to prostaglandins, is (5Z)-9-deoxy-6,9α-epoxy-Δ$^5$-PGF$_1$ and is represented by the formula

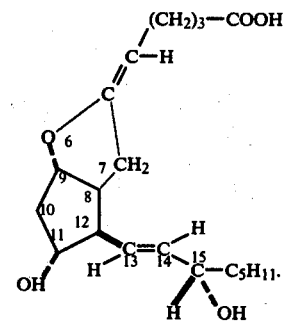

For its synthesis and structure see for example R. A. Johnson et al. J. Am. Chem. Soc. 99, 4182 (1977) and Prostaglandins 12, 915 (1976), and E. J. Corey et al., cited above. For some of its biological properties and uses see the references cited in the Johnson references. Prostacyclin is referred to as "PGI$_2$", see Anonymous, Prostaglandins 13, 375 (1977).

SUMMARY OF THE INVENTION

It is the purpose of this invention to provide novel products having pharmacological activity. It is a further purpose to provide processes for preparing these products and their intermediates.

Accordingly, there is provided a compound of the formula:

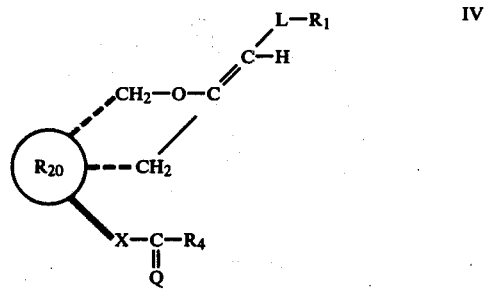

or a mixture comprising that compound and the enantiomer thereof wherein $R_{20}$ is

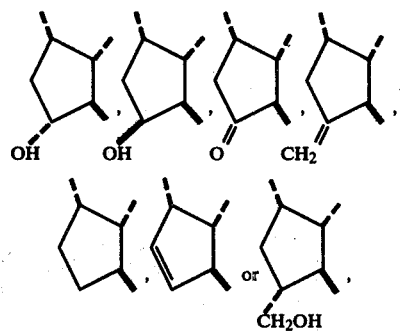

wherein L is
 (1) —(CH$_2$)$_d$—C(R$_2$)$_2$—
 (2) —CH$_2$—O—CH$_2$—Y— or
 (3) —CH$_2$CH=CH—
wherein d is zero to 5, R$_2$ is hydrogen, methyl, or fluoro, being the same or different with the proviso that one $R_2$ is not methyl when the other is fluoro, and Y is a valence bond, —$CH_2$— or —$(CH_2)_2$—,
wherein Q is

wherein $R_8$ is hydrogen or alkyl of one to 4 carbon atoms, inclusive,
wherein $R_1$ is
(1) —$COOR_3$
(2) —$CH_2OH$
(3) —$CH_2N(R_9)(R_{18})$

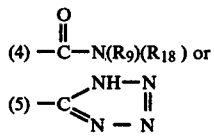

wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

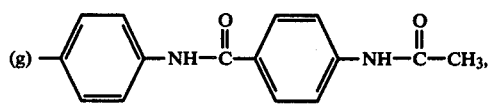

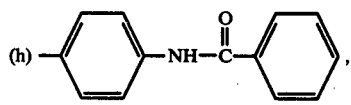

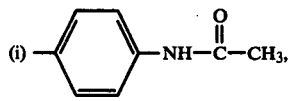

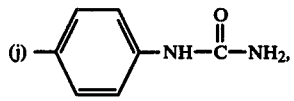

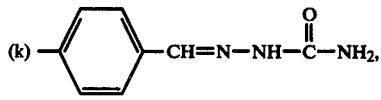

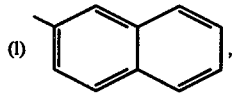

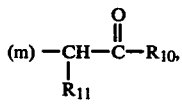

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_9$ is hydrogen, methyl, or ethyl, and $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;
wherein $R_4$ is

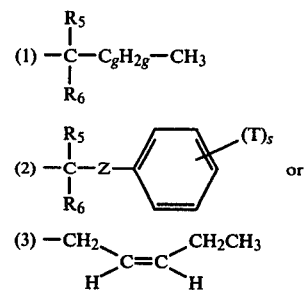

wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_8$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the phenyl ring; wherein T is alkyl of one to 4 carbon atoms, inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different; and
wherein X is
(1) trans—CH=CH—
(2) cis—CH=CH—
(3) —C≡C— or
(4) —$CH_2CH_2$—;
including the lower alkanoates thereof.

In formula IV as used herein, attachment to $R_{20}$ and $R_{21}$ corresponds to bonds to the cyclopentane ring at the C-8, C-9, and C-12 positions following prostaglandin nomenclature, thus:

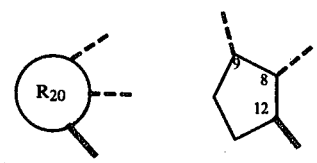

Within the scope of the prostaglandin derivatives described herein there are represented
(a) $PGF_\alpha$ compounds when $R_{20}$ is

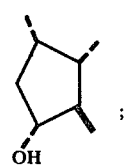

(b) 11β-$PGF_\alpha$ compounds when $R_{20}$ is (c) 11-Deoxy-11-keto-PGF$_\alpha$ compounds when ⓡ$_{20}$ is

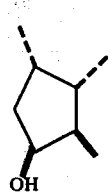

(d) 11-Deoxy-11-methylene-PGF$_\alpha$ compounds when ⓡ$_{20}$ is

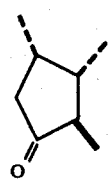

(e) 11-Deoxy-PGF$_{60}$ compounds when ⓡ$_{20}$ is

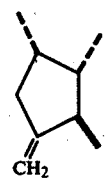

(f) 11-Deoxy-10,11-Didehydro-PGF$_\alpha$ compounds when ⓡ$_{20}$ is

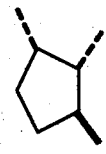

(g) 11-Deoxy-11-hydroxymethyl-PGF$_\alpha$ compounds when ⓡ$_{20}$ is

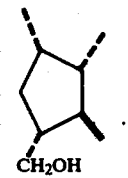

For those compounds of formula IV wherein Q is

i.e. wherein the C-15 hydroxyl group is attached to the side chain in alpha configuration, the configuration at C-15 is identical with that of the naturally occuring prostaglandins such as PGE$_1$ obtained from mammalian tissues. The 15-epimer compounds are represented by formula IV when Q is

and are identified variously as "15-epi" or "15β" or "15R" by the appropriate prefix in the name. As is known in the art, "R" and "S" designations depend on the neighboring substituents. See R. S. Cahn, J. Chem. Ed. 41, 116 (1964).

I claim:
1. A 5E compound of the formula

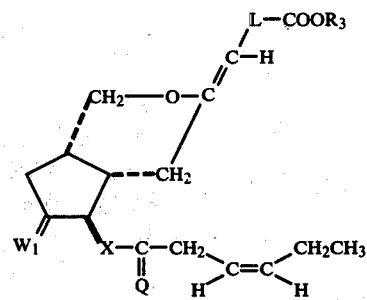

wherein W$_1$ is α—OH:β—H, α—H:β—OH, oxo, methylene, α—H:β—H, α—CH$_2$OH:β—H;
wherein L is
(1) —(CH$_2$)$_d$—C(R$_2$)$_2$,
(2) —CH$_2$—O—CH$_2$—Y—, or
(3) —CH$_2$CH=CH—,
wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein Q is oxo, α—H:β—H, α—OH:β—R$_8$ or α—R$_8$:β—OH
wherein R$_8$ is hydrogen or alkyl of one to 4 carbon atoms, inclusive,
wherein R$_3$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl of one to 4 carbon atoms, inclusive,
(g) p-[p-(acetamido)benzamido]phenyl,
(h) p-benzamidophenyl,
(i) p-acetamidophenyl,
(j) p-phenylurea,
(k) p-benzaldehyde semicarbazone,
(l) β-naphthyl,
(m) CH(R$_{11}$)—CO—R$_{10}$,
wherein R$_{10}$ is phenyl, p-bromophenyl, p-biphenylyl, p-nitrophenyl, p-benzamidophenyl, or 2 naphthyl, and wherein R$_{11}$ is hydrogen or benzoyl, or
(n) a pharmacologically acceptable cation;
wherein X is
(1) trans—CH=CH—,
(2) cis—CH=CH—,
(3) —C≡C—, or
(4) —CH$_2$CH$_2$—;
including the lower alkanoates thereof.
2. A 5Z compound of the formula

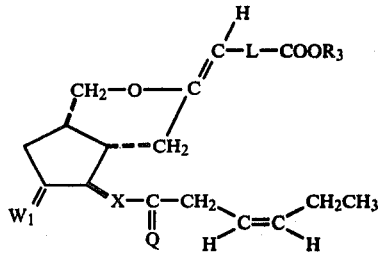

wherein $W_1$ is $\alpha$—OH:$\beta$—H, $\alpha$—H:$\beta$—OH, oxo, methylene, $\alpha$—H:$\beta$—H, $\alpha$—CH$_2$OH:$\beta$—H;

wherein L is
  (1) —(CH$_2$)$_d$—C(R$_2$)$_2$,
  (2) —CH$_2$—O—CH$_2$—Y—, or
  (3) —CH$_2$CH=CH—, wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—, wherein Q is oxo, $\alpha$—H:$\beta$—H, $\alpha$—OH:$\beta$—R$_8$ or $\alpha$—R$_8$:$\beta$—OH wherein R$_8$ is hydrogen or alkyl of one to 4 carbon atoms, inclusive, wherein R$_3$ is
  (a) hydrogen,
  (b) alkyl of one to 12 carbon atoms, inclusive,
  (c) cycloalkyl of 3 to 10 carbon atoms, inclusvie,
  (d) aralkyl of 7 to 12 carbon atoms, inclusive,
  (e) phenyl,
  (f) phenyl substituted with one, 2, or 3 chloro or alkyl of one to 4 carbon atoms, inclusive,
  (g) p-[p-(acetamido)benzamido]phenyl,
  (h) p-benzamidophenyl,
  (i) p-acetamidophenyl,
  (j) p-phenylurea,
  (k) p-benzaldehyde semicarbazone,
  (l) $\beta$-naphthyl,
  (m) CH(R$_{11}$)—CO—R$_{10}$, wherein R$_{10}$ is phenyl, p-bromophenyl, p-biphenylyl, p-nitrophenyl, p-benzamidophenyl, or 2 naphthyl, and wherein R$_{11}$ is hydrogen or benzoyl, or
  (n) a pharmacologically acceptable cation;
wherein X is
  (1) trans—CH=CH—,
  (2) cis—CH=CH—,
  (3) —C≡C—, or
  (4) —CH$_2$CH$_2$—;
including the lower alkanoates thereof.

3. (5Z)-9-Deoxy-6,9$\alpha$-epoxymethano-$\Delta^5$-17,18-cis-didehydro-PGF$_1$, sodium salt, or (5Z)-9-deoxy-6,9$\alpha$-epoxymethano-$\Delta^5$-17,18-cis-didehydro-PGF$_1$, methyl ester, compounds according to claim 2.

4. A compound according to claim 1 or 2, wherein $W_1$ is $\alpha$—H:$\beta$—OH.

5. A compound according to claim 1 or 2, wherein $W_1$ is oxo.

6. A compound according to claim 1 or 2, wherein $W_1$ is methylene.

7. A compound according to claim 1 or 2, wherein $W_1$ is $\alpha$—H:$\beta$—H.

8. A compound according to claim 1 or 2, wherein $W_1$ is $\alpha$—CH$_2$OH:$\beta$—H.

9. A compound according to claim 1 or 2, wherein $W_1$ is $\alpha$—OH:$\beta$—H.

10. A compound according to claim 9, wherein L is —(CH$_2$)$_n$—, n being 3, 4, or 5, wherein Q is oxo or $\alpha$—OH:$\beta$—R$_8$ and wherein R$_8$ is hydrogen, methyl, or ethyl.

11. A compound according to claim 10, wherein X is —C≡C—.

12. A compound according to claim 10, wherein X is —CH$_2$CH$_2$—.

13. A compound according to claim 10, wherein X is trans—CH=CH—.

14. A compound according to claim 13, wherein R$_3$ is p-substituted phenyl.

15. A compound according to claim 13, wherein R$_3$ is CH(R$_{11}$)—CO—R$_{10}$.

16. A compound according to claim 13, wherein R$_3$ is hydrogen, alkyl of one to 12 carbon atoms, inclusive, or a pharmacologically acceptable cation.

17. A compound according to claim 13, wherein R$_3$ is hydrogen, methyl, or a pharmacologically acceptable cation.

* * * * *

UNITED STATES PATENT OFFICE
CERTIFICATE OF CORRECTION

Patent No. 4,200,739          Dated 29 April 1980

Inventor(s) Robert C. Kelly

It is certified that error appears in the above-identified patent and that said Letters Patent are hereby corrected as shown below:

Column 4, line 40, "(3) -C=C-" should read -- (3) -C≡C- --; line 45, "and $R_2$" should be deleted;

Column 6, line 65, "(3) -C=C-" should read -- (3) -C≡C- --.

*Signed and Sealed this*

*Twenty-seventh* Day of *January 1981*

[SEAL]

*Attest:*

RENE D. TEGTMEYER

*Attesting Officer*     *Acting Commissioner of Patents and Trademarks*